United States Patent [19]
Ortiz, Jr.

[11] Patent Number: 6,046,802
[45] Date of Patent: Apr. 4, 2000

[54] OPTICAL ELEMENT SURFACE MONITORING SYSTEM AND METHOD

[75] Inventor: Angel Luis Ortiz, Jr., Ballston Spa, N.Y.

[73] Assignee: General Electric Company, Schenectady, N.Y.

[21] Appl. No.: 09/192,693

[22] Filed: Nov. 16, 1998

[51] Int. Cl.[7] .................................................. G01N 21/55
[52] U.S. Cl. ............................................................ 356/237.1
[58] Field of Search ................................. 356/124, 237.1

[56] References Cited

U.S. PATENT DOCUMENTS

| | | | |
|---|---|---|---|
| H376 | 12/1987 | Bremer | 356/237.1 |
| 4,385,832 | 5/1983 | Doi et al. | 356/73.1 |
| 4,423,726 | 1/1984 | Imagawa et al. | 219/121 |
| 5,159,402 | 10/1992 | Ortiz | 356/237.1 |
| 5,323,269 | 6/1994 | Walker et al. | 359/739 |

*Primary Examiner*—Richard A. Rosenberger
*Attorney, Agent, or Firm*—Marvin Snyder; Douglas E. Stoner

[57] ABSTRACT

An optical element surface monitoring system includes an optical beam shaper and an optical sensor. The optical beam shaper directs an input beam of light from a laser source onto a surface portion of an optical element. The optical sensor receives a reflected beam of light from the optical element, derived from the input beam of light. The power of the reflected beam of light is monitored for an unexpected dropoff as an indicator of damage to the surface portion.

20 Claims, 9 Drawing Sheets

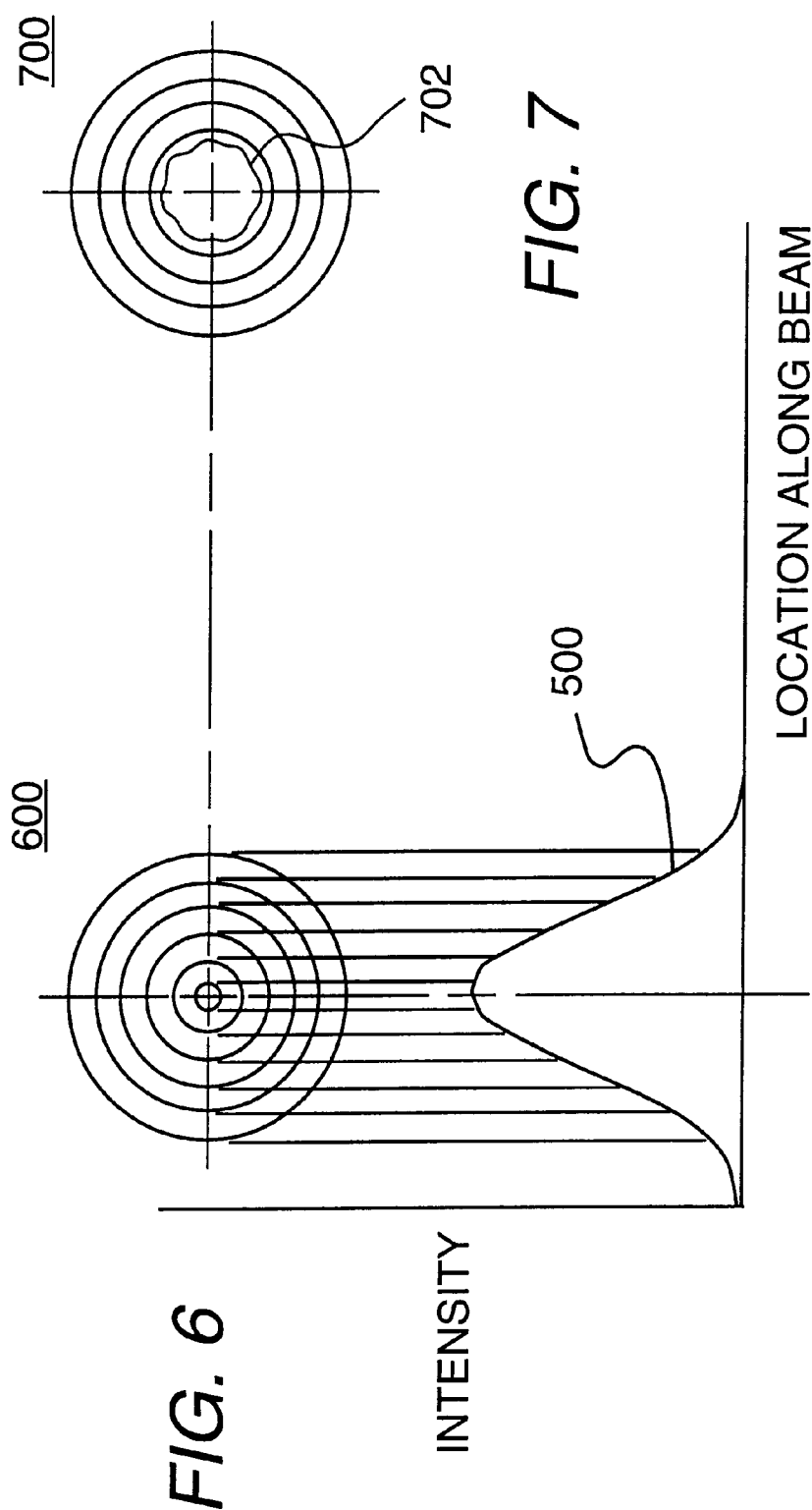

OPTICAL ELEMENT SURFACE MONITORING SYSTEM AND METHOD

The U.S. Government has a paid-up license in this invention and the right in limited circumstances to require the patent owner to license others on reasonable terms as provided for by the terms of Government Contract No. MDA972-94-30020 awarded by DARPA.

FIELD OF THE INVENTION

This invention relates, generally, to laser systems and, more particularly, to optical elements for use in laser systems.

BACKGROUND OF THE INVENTION

In laser systems, it can be expensive in terms of cost of acquiring material resources and time for production of the same, to replace certain optical elements such as non-linear optical crystals used for frequency conversion.

For example, a beam of light from a laser source may pass through a beam shaping system (e.g., a lens), and may impinge upon a crystal. In particular, the beam shaping system may focus the beam of light to form a waist, at which may be located the crystal. Typically, the laser system is designed with an expectation of successful performance of the crystal located within the waist of the beam of light. However, should the fluence, that is, the energy per unit area (e.g., Joules per square centimeter), exceed a certain limit for the crystal, the crystal is likely to suffer damage.

When the crystal is originally placed in the path of the laser beam, observation of system success or failure can reveal whether the crystal suffers catastrophic failure, such as bulk fractures. If the crystal is damaged immediately, the laser beam diameter on the crystal may then be enlarged to reduce the fluence on a replacement crystal and thereby reduce the likelihood of immediate damage to the replacement crystal.

However, once a crystal has been operating in the laser system, the laser system might continue to operate regardless of any degree of damage to the crystal until the crystal suffers catastrophic failure such as bulk fractures, at which point replacement of the crystal would undesirably be required. Such replacement of the crystal can entail relatively large expenditure for material, and relatively lengthy downtime (e.g., two, three, or four months of crystal growth time) should a substitute crystal not readily be available.

Thus, a need exists for a system for monitoring the surface of an optical element (e.g., a non-linear crystal in a laser system) to detect damage to the surface prior to catastrophic failure, such as bulk fractures in the optical element. Such system should also be capable of detecting initiation of damage to the surface of the optical element. The system should allow repair of the surface damage so as to permit continued operation of the optical element (e.g., in a laser system).

SUMMARY OF THE INVENTION

In one aspect of the invention, an optical element surface monitoring system includes an optical beam shaper and an optical sensor. The optical beam shaper directs an input beam of light from a laser source onto a surface portion of an optical element. The optical sensor receives a reflected beam of light from the optical element. The reflected beam of light is derived from the input beam of light. The reflected beam of light is monitored for an unexpected variation therein as an indicator of damage to the surface portion.

Another aspect of the invention contemplates an optical element surface monitoring method wherein a beam of light reflected from an optical element is monitored for an unexpected variation. The reflected beam of light is derived from an input beam of light from a laser directed onto a surface portion of the optical element. Detection of the unexpected variation is employed to indicate damage to the surface portion.

BRIEF DESCRIPTION OF THE DRAWINGS

FIG. 5 is one example of a graph of intensity versus location along an axis of a beam of light provided by a laser source;

FIG. 6 is one example of a laser diagnostics spatial profile of a reflected beam of light derived from the beam of light of FIG. 5, illustrating an exemplary good state for a crystal serving as a reflective surface;

FIG. 7 is similar to FIG. 6 and illustrates an exemplary condition of damage to the surface of the crystal;

DETAILED DESCRIPTION

Figure 1:
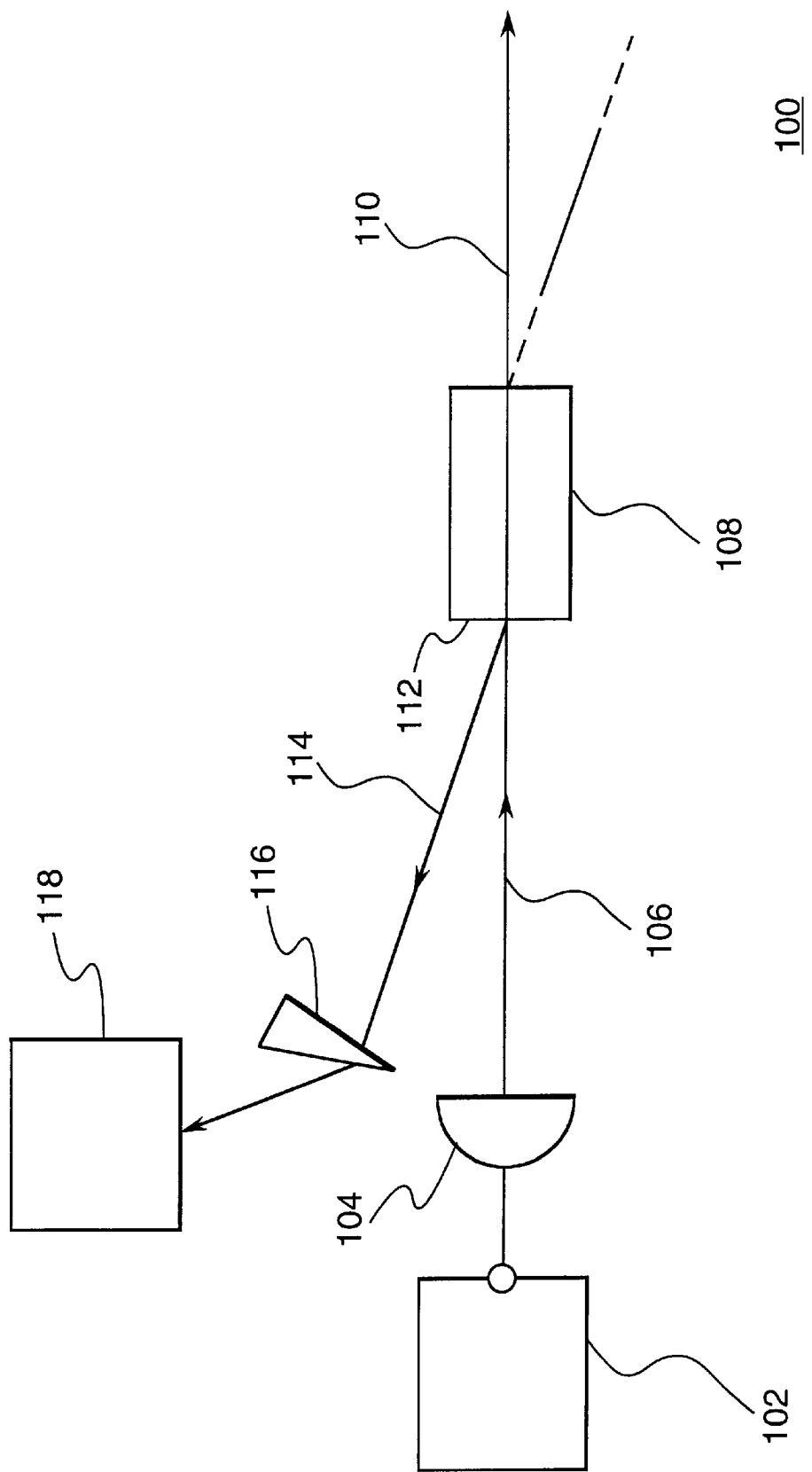
FIG. 1 is a schematic diagram of one example of a laser system configured to monitor surface integrity of a crystal.

In FIG. 1, a laser system 100 includes a laser source 102 optically coupled to a beam shaper 104 that directs a fundamental beam of light 106 onto an optical element 108. For instance, the laser source may comprise a high-powered, gas, solid-state crystal, glass, or semiconductor laser. Also, as an example, the beam shaper may comprise a lens. The optical element may comprise, for example, a non-linear, (e.g., anti-reflective) coated, or uncoated crystal. As another example, the optical element may comprise a lens.

Beam shaper 104 may serve to focus fundamental beam of light 106 on optical element 108. If the optical element comprises a non-linear crystal, it may be employed for frequency conversion. For instance, the optical element may be employed for any kind of harmonic (e.g., second, third, or fourth harmonic) generation or optical parametric oscillation. Exemplary non-linear crystals include lithium triborate ("LBO") and other crystals based on boron (e.g., "BBO") or potassium (e.g., "KTP," "KT*P"). In one aspect, such materials may be used separately or in combination for generating different wavelengths from a fundamental wavelength, as will be understood by those skilled in the art. Nevertheless, the invention as described herein may be employed with any optical element in any laser system.

Fundamental beam of light 106 supplied to optical element 108 may have a fundamental wavelength of, e.g., 1064 nm (for neodymium doped yttrium aluminum garnet, or Nd:YAG). By injecting the fundamental beam of light into a non-linear crystal, a second wavelength may be generated (e.g., 532 nm "green," for example) which may depend upon the frequency conversion, the kind of crystal, and/or the type of crystal cut in the lattice. Namely, the process of frequency conversion is a non-linear process. Furthermore, output light 110 from optical element 108 may comprise a first beam of light exhibiting the fundamental wavelength, and a second beam of light exhibiting the second wavelength, with each beam tending to exit the crystal at a slightly different angle, since the index of refraction is different for the two different wavelengths.

Fundamental beam of light 106 impinging upon optical surface 112 of optical element 108 produces a Fresnel reflection 114, due to a change in refractive index between the crystal surface and a surrounding atmosphere (e.g., air, helium, etc.). In one example, optical surface 112 may include an anti-reflective ("AR") coating, depending upon factors such as application of the crystal and/or amount of power provided by laser source 102. Crystals with AR coating (e.g., dielectric coatings) have previously been employed to reduce the amount of Fresnel reflections, so as to avoid extraneous light signals and/or power interference in laser systems employing such crystal. In one aspect of the invention, Fresnel reflection 114 is advantageously employed to monitor integrity of optical surface 112, with or without AR coating.

A beam director 116 receives Fresnel reflection 114 from optical surface 112 and directs the Fresnel reflection to optical sensor 118. In one example, the beam director comprises a prism which is positioned once a Fresnel reflection has been located, and which may be employed for directing the Fresnel reflection to the optical sensor regardless of movement or change of optical element 108 within a certain range. For instance, the optical sensor may comprise a photodiode, power meter, or laser beam diagnostics system. Also, in a further example, Fresnel reflection 114 may result from angle-tuning for enhancing performance of a crystal such as optical element 108.

Figure 2:
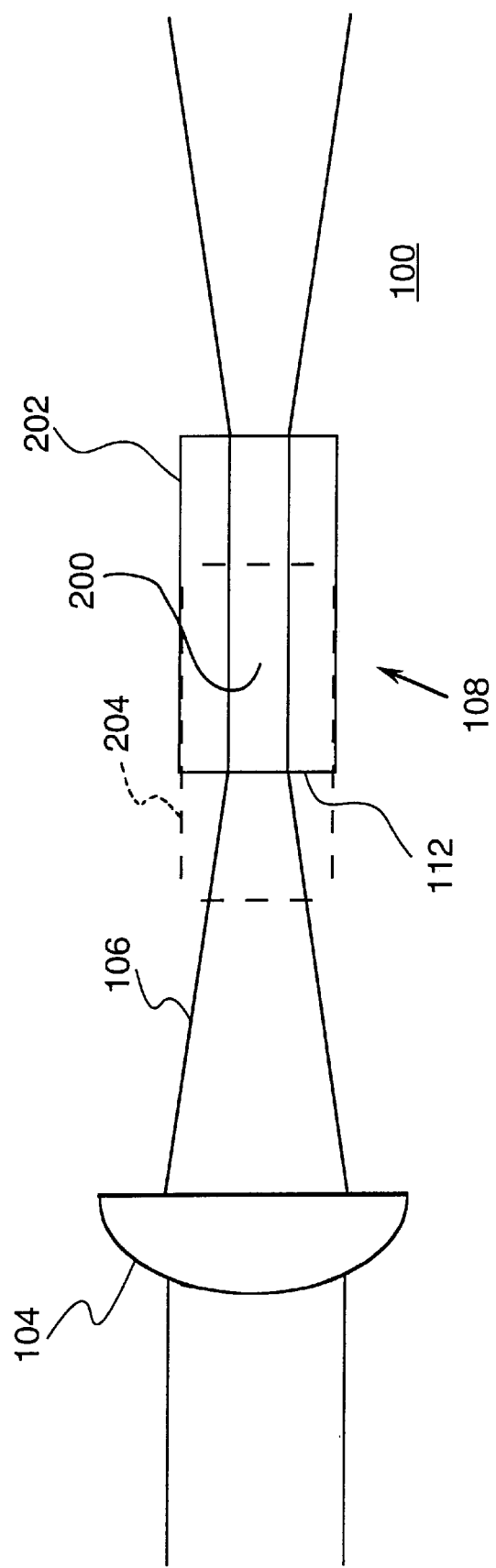
FIG. 2 is a schematic diagram of a lens shaping a beam of light from a laser source to the crystal of FIG. 1, illustrating various locations for the crystal.

Optical element 108, as shown in FIG. 2, may occupy any of various locations relative to waist 200 of fundamental beam of light 106, such as location 202 and location 204. For example, if optical surface 112 receives too much energy from the fundamental beam of light at location 202 for a certain beam diameter (e.g., beam diameter 902 discussed below with reference to FIG. 9), then the optical element may be moved, for instance, to location 204 so that the beam diameter is increased at optical surface 112. In this manner, the same amount of power is spread over a larger area, reducing the fluence and thereby diminishing chances of damage to optical surface 112 and bulk damage to the optical elements. However, one downside of reducing the fluence on a non-linear crystal is a reduction of conversion efficiency.

Figure 3:
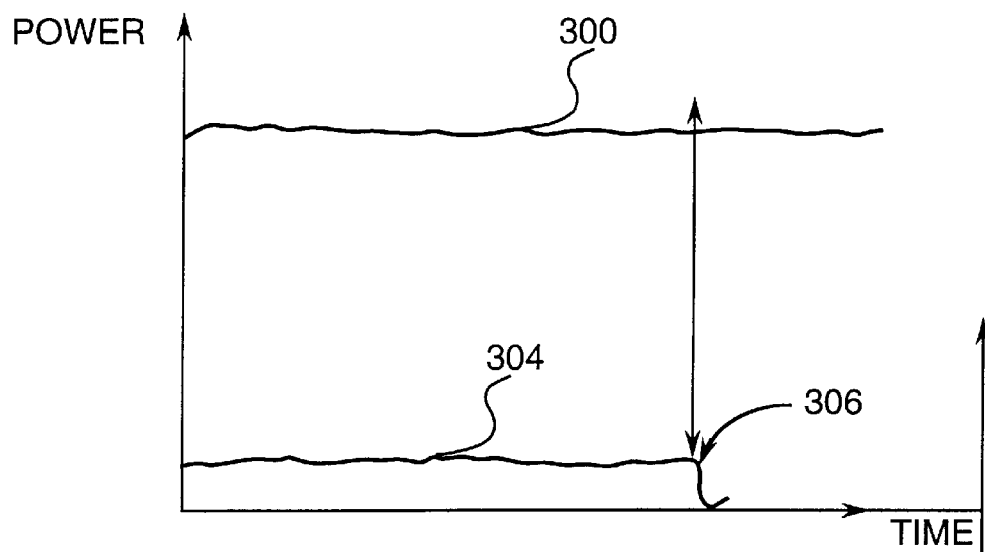
FIG. 3 is a graph of laser power and Fresnel reflection plotted versus time, illustrating an exemplary detection of initiation of damage to a surface of the crystal of FIG. 1.

Referring to FIGS. 1 and 3 for purposes of illustration, laser source 102 may be considered to produce fundamental beam of light 106 having relatively constant power, as represented by plot 300 of FIG. 3. The power produced by the laser source may be monitored with a power meter such as may be found in typical lasers. Plot 304 of FIG. 3 serves to illustrate that Fresnel reflection 114 may exhibit fairly constant power under usual operation, until optical surface 112 experiences initiation of damage, as represented by a dropoff 306 of plot 304. Fresnel reflection 114 may be monitored by directing the reflection to optical sensor 118 through beam director 116. In typical operation, the Fresnel reflection may be fairly constant at about 4.0% of the total power of the fundamental beam of light impinging upon an uncoated portion of optical surface 112, or 0.2% of the total power of the fundamental beam of light impinging upon a coated portion of optical surface 112. The dropoff 306 may be explained by scattering of the Fresnel reflection 114, which is detected by optical sensor 118 as a decline in intensity of the sensed signal owing to the scattering caused by damage to optical surface 112.

Figure 4:
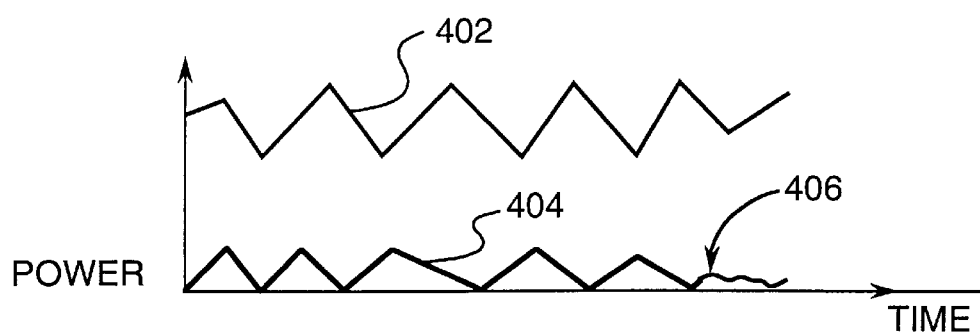
FIG. 4 is similar to FIG. 3 and depicts another exemplary detection of initiation of damage to a surface of the crystal.

Referring to FIGS. 1 and 4, plot 402 of FIG. 4 represents power of fundamental beam of light 106, which varies over time with coordinated or correlated varying of plot 404 representing power of Fresnel reflection 114 varying over time. In particular, a number of dropoffs occur in plots 402 and 404, but an initiation of damage is not indicated until dropoff 406. In particular, dropoff 406 represents a decline in power not coordinated or correlated with any dropoff in plot 402, owing to scattering of Fresnel reflection 114 because of initiation of damage to optical surface 112.

Considering FIGS. 5–7 in conjunction with FIG. 1, plot 500 represents an intensity profile for Fresnel reflection 114, which for explanatory purposes may be considered to be correlated with an intensity profile for fundamental beam of light 106. Spatial profile 600 represents information of plot 500 depicted along two axes, for a good condition of optical surface 112. Spatial profile 700 represents a condition of damage to optical surface 112 resulting from a scattering of Fresnel reflections from optical surface 112 owing to (e.g., severely) compromised integrity thereof. Degradation of spatial profile 700 can be seen in exemplary region 702. In one example, such as where optical sensor 118 comprises a laser beam diagnostics system, a depiction of degradation in spatial profile 600 for Fresnel reflection 114 uncorrelated with a variation in fundamental beam of light 106 may advantageously be employed to signal initiation of damage to optical surface 112. Detection of initiation of damage to optical surface 112 may be employed to stop the fundamental beam of light from impinging on optical surface 112, so that the optical surface may be inspected and/or repaired. Where optical element 108 comprises a crystal, the crystal may be inspected optically, such as with a high-powered microscope (not shown). Should the crystal be damaged, it may be removed from laser system 100, so that optical surface 112 may be polished (e.g., provided with an acid etch to remove any coating, followed by a mechanical polish, using an optical polisher), the optical surface may be coated if desired, and the crystal may be returned to the laser system. Desirably, this technique is less expensive and more efficient than the previous approach of substituting a new crystal for a crystal damaged beyond repair or restoration because of previous failure to detect initiation of damage to the crystal surface. As will be appreciated by those skilled in the art, profiles other than the exemplary concentric ring spatial intensity profiles illustrated in FIGS. 6–7 are possible, for example, top hat and doughnut modes.

Figure 8:
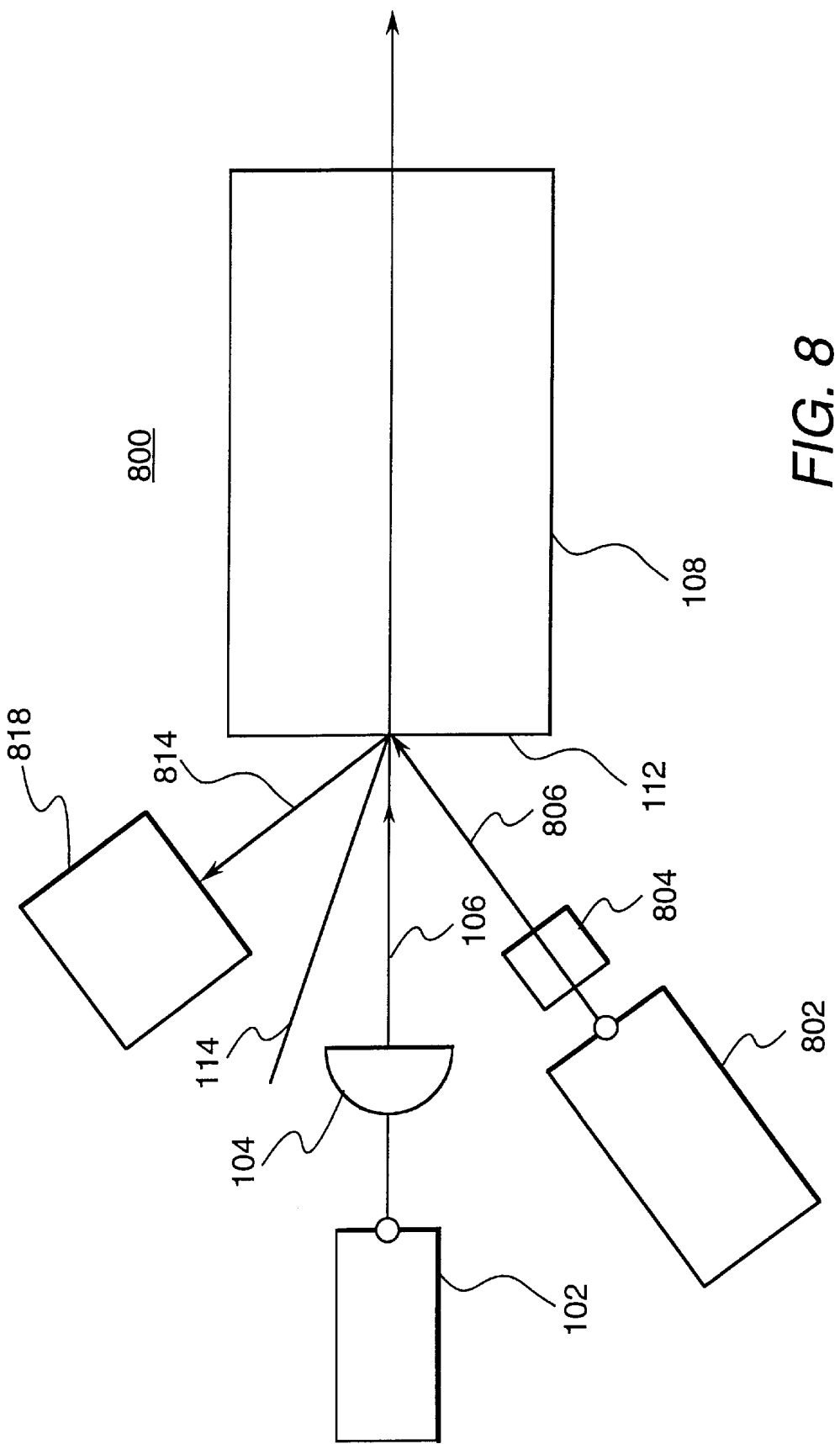
FIG. 8 is a schematic diagram of another example of a laser system configured to monitor surface integrity of a crystal, illustrating use of a probe laser.

A laser system 800, shown in FIG. 8, includes a probe laser 802 and an optical beam shaper 804, such as a lens, directing a probe beam of light 806 onto optical surface 112 of optical element 108. Laser system 800 may include or omit features described herein with reference to laser system 100 of FIG. 1. A reflected beam of light 814, derived from probe beam of light 806, may be received by an optical sensor 818 similar to optical sensor 118 illustrated in FIG. 1. In another aspect, monitoring of the reflected beam of light with respect to the probe beam of light may serve to detect initiation of damage to optical surface 112. That is, the techniques described herein with respect to monitoring of Fresnel reflection 114 derived from fundamental beam of light 106 may be analogously applied and/or extended to monitoring of reflected beam of light 814 derived from probe beam of light 806. For instance, a baseline can be established for an input beam of light and a reflected beam of light derived therefrom can then be monitored for unexpected deviation, uncorrelation and/or uncoordination with respect to the input beam of light, as described herein.

Figure 9:
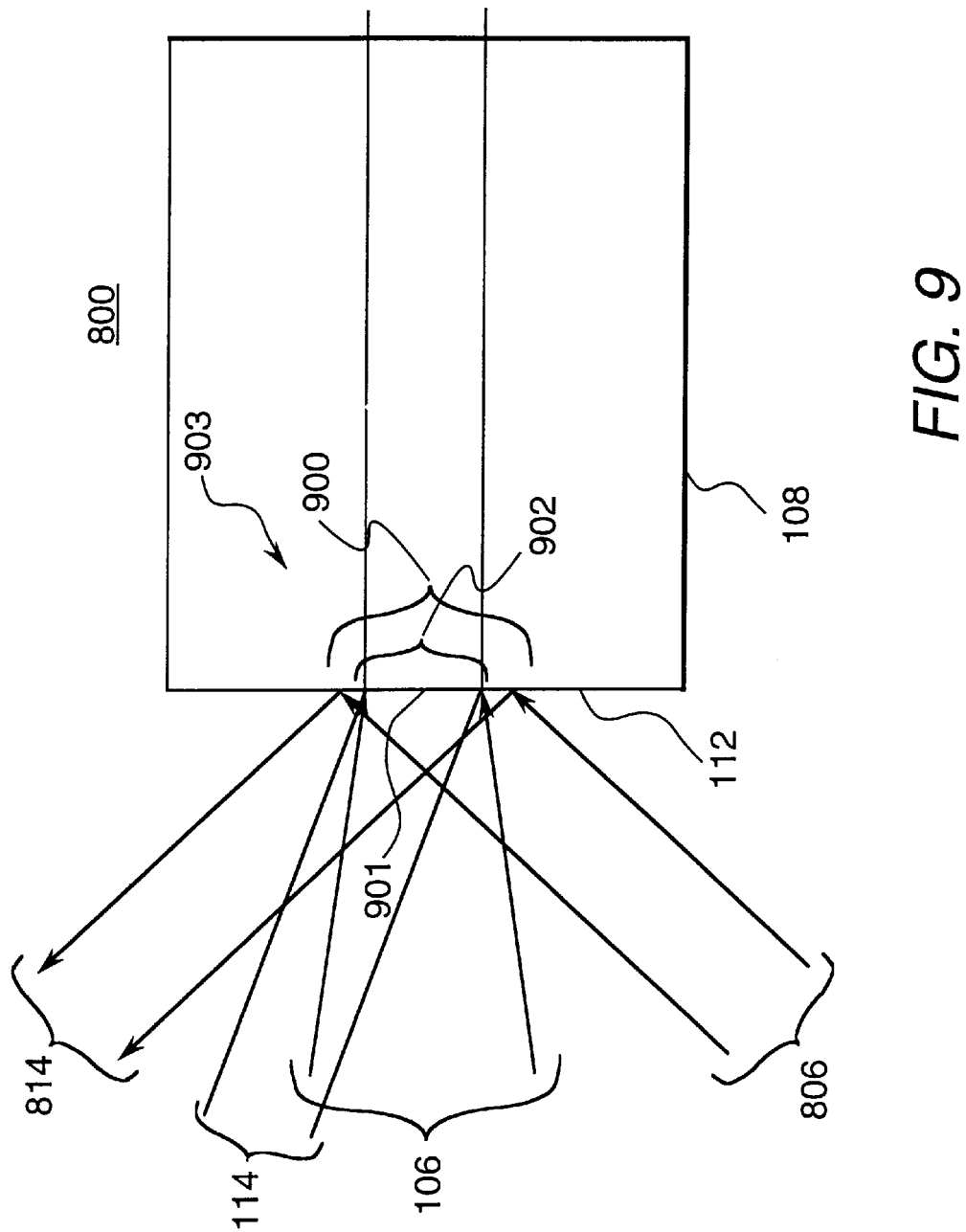
FIG. 9 is a schematic representation of a surface of the crystal of FIG. 8 and depicts a fundamental beam of light impinging upon the surface and a Fresnel reflection derived from the fundamental beam of light, and a probe beam of light impinging upon the surface and a reflected beam of light derived from the probe beam of light.

In FIG. 9, as one example, beam diameter 900 for probe beam of light 806 at region 901 of optical surface 112 is made larger than beam diameter 902 for fundamental beam of light 106 at region 903 of optical surface 112. In this example, should the fundamental beam of light damage optical element 108 at optical surface 112, the damage will be located within beam diameter 902 for the fundamental beam of light. By making beam diameter 900 for the probe beam of light slightly larger than beam diameter 902 for the fundamental beam of light, laser system 800 remains capable of monitoring optical surface 112 notwithstanding any (e.g., temporal) instability which may cause relative movement between the optical surface and the probe beam of light or the fundamental beam of light. Thus, monitoring of the probe beam of light is a way of monitoring integrity of optical surface 112 by enabling avoidance of failure to observe damage to the optical surface. Alternatively, initiation of damage to optical surface 112 can be observed by techniques such as those described herein with reference to FIGS. 1 and 3–7, where a change or variation may be dramatic.

Figure 10:
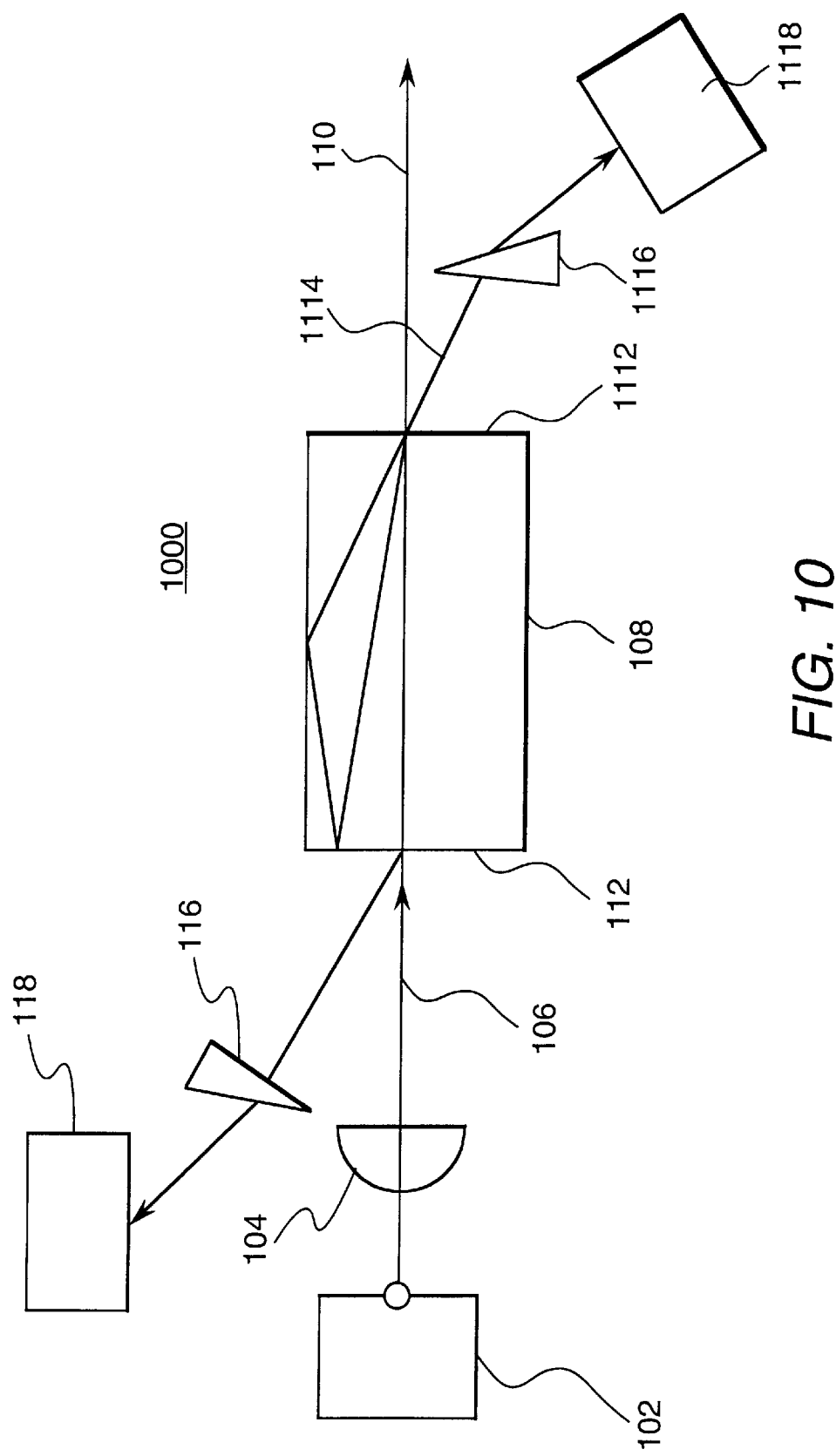
FIG. 10 is a schematic diagram of apparatus for monitoring multiple surfaces of a crystal with multiple reflected signals derived from a beam of light provided by a laser source.

In FIG. 10, a laser system 1000 resembles laser system 100 of FIG. 1, but includes a beam director 1116 and optical sensor 1118 for monitoring optical surface 1112 of optical element 108 by employing a Fresnel reflection 1114. The Fresnel reflection may be derived from fundamental beam of light 106, as will be understood by those skilled in the art.

Figure 11:
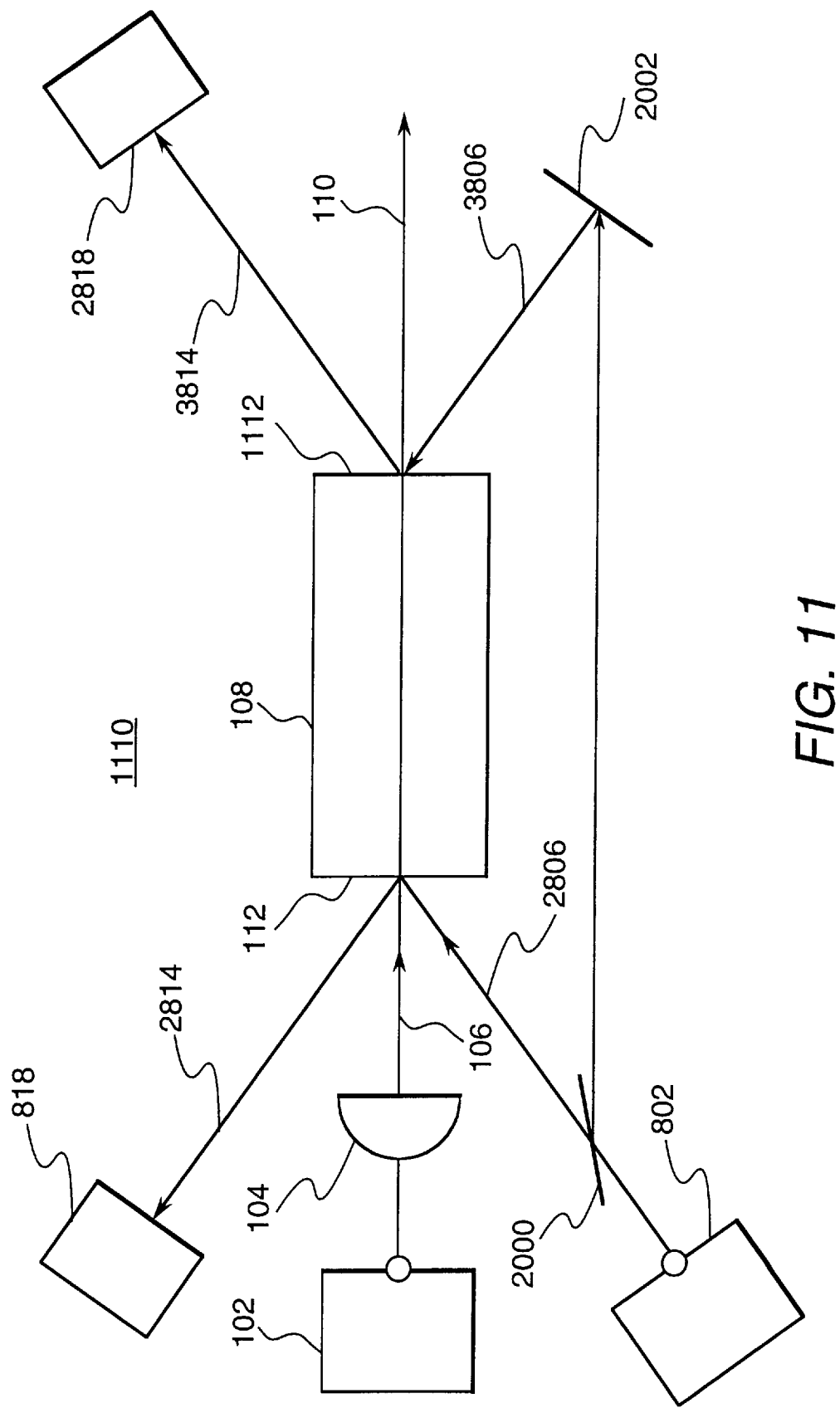
FIG. 11 is a schematic diagram of another example of a configuration for monitoring multiple surfaces of a crystal through use of a probe laser, a beam splitter and a mirror.

In FIG. 11, a laser system 1110 resembles laser system 800 of FIG. 8, but includes a beam splitter 2000, mirror 2002, and an optical sensor 2818. Probe laser 802 is optically coupled to the beam splitter to provide a probe beam of light 2806 directed onto optical surface 112 of optical element 108 and to provide a probe beam of light 3806 directed by mirror 2002 onto optical surface 1112 of optical element 108. Optical sensor 818 receives a reflected beam of light 2814 to monitor integrity of the optical surface 112, and optical sensor 2818 receives a reflected beam of light 3814 to monitor integrity of optical surface 1112.

Figure 12:
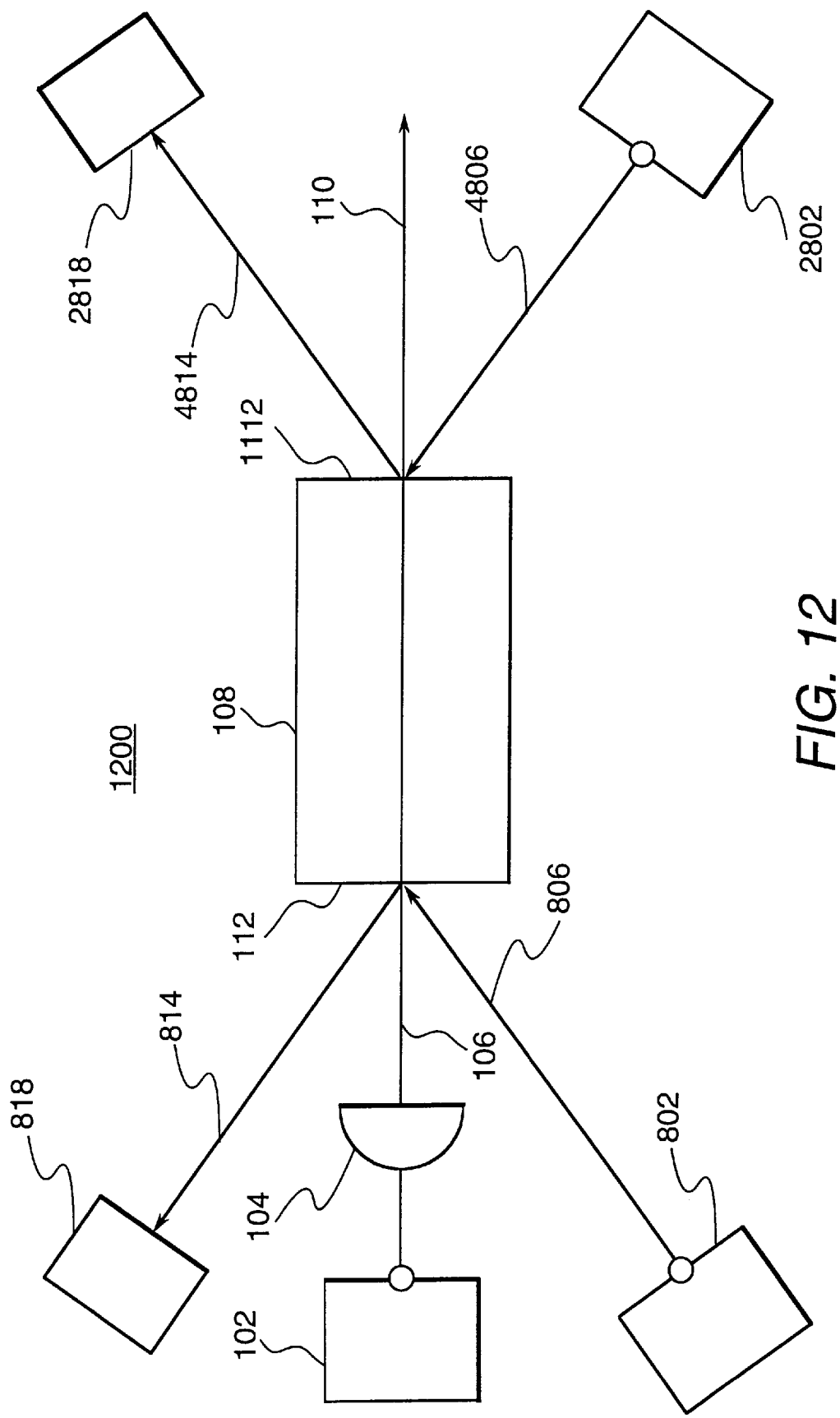
FIG. 12 is a schematic diagram of a configuration for monitoring multiple surfaces of a crystal through use of multiple probe lasers.

In FIG. 12, a laser system 1200 resembles laser system 800 of FIG. 8, but includes a probe laser 2802 and optical sensor 2818. Probe laser 2802 provides a probe beam of light 4806 that impinges upon optical surface 1112, where a reflected beam of light 4814 derived from probe beam of light 4806 may be monitored by optical sensor 2818 to monitor integrity of optical surface 1112.

While only certain preferred features of the invention have been illustrated and described, many modifications and changes will occur to those skilled in the art. It is, therefore, to be understood that the appended claims are intended to cover all such modifications and changes as fall within the true spirit of the invention.

I claim:

1. An optical crystal surface monitoring system, comprising:

a first optical beam shaper for directing an input beam of light from a laser source to a surface portion of an optical crystal; and an optical sensor for receiving a beam of light Fresnel reflected from said optical crystal and derived from said input beam of light, wherein an unexpected dropoff in intensity of the reflected beam of light at the sensor resulting from spatial profile degradation of the Fresnel reflected light beam is a result of damage to the surface portion of said optical crystal.

2. The system of claim 1, wherein said optical sensor is adapted to provide an indication of said unexpected dropoff in intensity of the reflected beam of light when said dropoff is unaccompanied by a correlating dropoff in power of said input beam of light.

3. The system of claim 1, wherein said optical sensor comprises one of the group consisting of a photodiode, a photodetector, a power meter, and a laser beam diagnostics system.

4. The system of claim 1, wherein said optical crystal comprises one of the group consisting of a coated crystal and an uncoated crystal.

5. The system of claim 1, further comprising a beam director located between said surface portion and said optical sensor to direct said reflected beam of light to said optical sensor.

6. The system of claim 1, further comprising:

a probe laser; and a second optical beam shaper for directing a second beam of light from said probe laser to a part of said surface portion of said optical crystal illuminated by said input beam of light.

7. The system of claim 6, wherein said first optical beam shaper is adapted to provide said input beam of light with a first beam diameter at said surface portion, wherein said second optical beam shaper is adapted to provide said second beam of light with a second beam diameter at said part of said surface portion, and wherein said second beam diameter is larger than said first beam diameter.

8. The system of claim 6, wherein said part of said surface portion is generally centered relative to said surface portion.

9. The system of claim 1, and further comprising:

a second optical sensor for receiving a second Fresnel reflected beam of light from said optical crystal, said second optical sensor being optically coupled with a second surface portion of said optical element, wherein said second optical sensor is adapted to provide an indication of an unexpected dropoff in intensity of said second reflected beam of light at the second sensor resulting from spatial profile degradation of the second Fresnel reflected light beam as an indicator of damage to said second surface portion.

10. The system of claim 9, further including a probe laser for producing a second input beam of light directed onto said second surface portion, said second reflected beam of light being derived from said second input beam of light.

11. An optical crystal surface monitoring method, comprising the steps of:

monitoring a Fresnel reflected beam of light from an optical crystal, said reflected beam of light being derived from a first input beam of light produced by a laser and directed onto a surface portion of said optical crystal; and detecting an unexpected dropoff in power of said reflected beam of light resulting from spatial profile degradation of the Fresnel reflected light beam as an indication of damage to said surface portion.

12. The method of claim 11, further comprising the step of:

halting impingement of said first input beam of light on said surface portion when said unexpected dropoff in power of said reflected beam is detected.

13. The method of claim 12 including a second input beam of light directed onto a part of said surface portion illuminated by said first input beam of light with greater beam diameter than said first input beam of light and further comprising the step of:

halting impingement of said second input beam of light on said surface portion when said unexpected dropoff in power of said reflected beam is detected.

14. The method of claim 13, further comprising the steps of:

repairing said surface portion after halting impingement of said first and second input beams of light on said surface portion; and directing said first and second input beams onto said surface portion after said surface portion has been repaired.

15. An optical crystal surface monitoring system, comprising:

a laser source;

a first optical beam shaper for directing an input beam of light from said laser source to a surface portion of an optical crystal; and an optical sensor for receiving a beam of light Fresnel reflected from said optical crystal and derived from said input beam of light, wherein an unexpected dropoff in intensity of the reflected beam of light at the sensor resulting from spatial profile degradation of the Fresnel reflected light beam is a result of damage to the surface portion of said optical crystal.

16. The system of claim 15, wherein said optical sensor is adapted to provide an indication of said unexpected dropoff in intensity of the reflected beam of light when said dropoff is unaccompanied by a correlating dropoff in power of said input beam of light.

17. The system of claim 15, further comprising a beam director located between said surface portion and said optical sensor to direct said reflected beam of light to said optical sensor.

18. The system of claim 15, and further comprising:

a probe laser; and a second optical beam shaper for directing a second beam of light from said probe laser to a part of said surface portion of said optical crystal illuminated by said input beam of light.

19. The system of claim 18, wherein said first optical beam shaper is adapted to provide said input beam of light with a first beam diameter at said surface portion, wherein said second optical beam shaper is adapted to provide said second beam of light with a second beam diameter at said part of said surface portion, and wherein said second beam diameter is larger than said first beam diameter.

20. A nonlinear optical element surface monitoring system, comprising:

a first optical beam shaper for directing an input beam of light from a laser source to a surface portion of an optical element;

an optical sensor for receiving a beam of light reflected from said optical element and derived from said input beam of light, wherein an unexpected dropoff in intensity of the reflected beam of light at the sensor is a result of damage to the surface portion of said optical element;

a probe laser; and a second optical beam shaper for directing a second beam of light from said probe laser to a part of said surface portion of said optical element illuminated by said input beam of light, wherein said first optical beam shaper is adapted to provide said input beam of light with a first beam diameter at said surface portion, wherein said second optical beam shaper is adapted to provide said second beam of light with a second beam diameter at said part of said surface portion, and wherein said second beam diameter is larger than said first beam diameter.

* * * * *